(12) United States Patent
Wright et al.

(10) Patent No.: US 9,006,371 B1
(45) Date of Patent: Apr. 14, 2015

(54) SYNTHESIS OF OLIGOMERIC SILSESQUIOXANE MONOMERS FOR HIGH PERFORMANCE POLYMERS

(75) Inventors: Michael E. Wright, Ridgecrest, CA (US); Brian J. Petteys, Salt Lake City, UT (US); Andrew J. Guenthner, Lancaster, CA (US); Sandra J. Tomczak, Lancaster, CA (US)

(73) Assignee: United States of America as Represented by the Secretary of the Navy, Washington, DC (US)

( * ) Notice: Subject to any disclaimer, the term of this patent is extended or adjusted under 35 U.S.C. 154(b) by 533 days.

(21) Appl. No.: 12/892,124

(22) Filed: Sep. 28, 2010

(51) Int. Cl.
*C08G 77/26* (2006.01)
*C07F 7/08* (2006.01)

(52) U.S. Cl.
CPC ................ *C07F 7/081* (2013.01); *C08G 77/26* (2013.01)

(58) Field of Classification Search
USPC ...................................................... 528/38, 26
See application file for complete search history.

(56) References Cited

U.S. PATENT DOCUMENTS

| | | | |
|---|---|---|---|
| 2,181,640 | A | 11/1939 | Deanesly et al. |
| 6,500,999 | B2 | 12/2002 | Di Girolamo et al. |
| 6,767,930 | B1 | 7/2004 | Svejda et al. |
| 6,933,345 | B1 | 8/2005 | Lichtenhan et al. |
| 7,619,042 | B2 | 11/2009 | Poe et al. |
| 2003/0232883 | A1* | 12/2003 | Jolidon et al. ................ 514/522 |

FOREIGN PATENT DOCUMENTS

JP          2005 232024     *  9/2005

OTHER PUBLICATIONS

JP 2005 232024 machine translation (2005).*
Leu et al., Synthesis and Dielectric Properties of Polyimide-Tethered Polyhedral Oligomeric Silsesquioxanes (POSS) Nanocomposites via (Macromolecules 2003, 36, 9122-27).
Leu et al. also describe an approach in "Polyimide-Side-Chain Tethered Polyhedral Oligomeric Silsesquioxane Nanocomposites for Low Dielectric Film Applications" Chemistr of.
Wright et al. article "Chemical Modification of Fluorinated Polyimides: New Thermally Curing Hybrid Polymers with POSS" (Macromolecules 2006, 39, pp. 4710-4718.
Wright et al. "The Synthesis of . . . " Chemistry of Materials 2003, vol. 15(1), pp. 264-270.

* cited by examiner

*Primary Examiner* — Kuo-Liang Peng
(74) *Attorney, Agent, or Firm* — Charlene A. Haley

(57) ABSTRACT

A formulation and methods for making formulation of a series of oligomeric silsesesquioxane (OS) diamine monomers which have been synthesized and purified in a highly time, energy, and atom efficient manner.

3 Claims, 5 Drawing Sheets

SYNTHESIS OF OLIGOMERIC SILSESQUIOXANE MONOMERS FOR HIGH PERFORMANCE POLYMERS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to the synthesis, purification, processing, and evaluation of aromatic diamines containing a class of oligomeric silsesquioxane (OS) moieties and presents examples of their use in preparing OS-polymeric materials with special focus on high molecular weight polyimides. These materials are critical for development and application to space exploration and use in other harsh environmental conditions found earth-bound.

BACKGROUND OF THE INVENTION

Diamines represent one of the most powerful and versatile class of monomers used in the commercial polymer business. Diamines are widely used in preparing polyimides, polyamides, and virtually all epoxy resins. The use of aromatic diamines is fundamental for preparation of high performance and temperature resistant polymeric materials. For polyimides perhaps one of the best known materials is Kapton® and this material has found widespread use in space applications. For polyamides, Kevlar® represents an aromatic polyamide that has found widespread use in fire-retardant clothing, armor, and many other applications. Thus, aromatic diamines are of great importance for creating thermally-stable/high-performance polymeric materials.

Although aromatic polymers can exhibit resistance to thermo-oxidative processes, it has been demonstrated that in the presence of atomic oxygen (AO) at high kinetic energies that virtually any and all carbon-carbon bonds are destroyed. Thus, Kapton® has been found to rapidly decompose when exposed to AO, both in a simulated environment and in actual low Earth orbit (LEO) testing. While thin coatings of metal oxides and other inorganic materials provide protection from AO erosion, they suffer from defects that occurring during their application along with cracking and failure due to a mismatch in coefficients of thermal expansion (CTE), impact, minor abrasions, or other typical wear and use scenarios. Once a crack appears, undercutting and acute failure of the coating begins leading to catastrophic polymer damage and then material failure.

Oligomeric silsesquioxanes (OS) can be incorporated into a polymer matrix to improve the resistance of the polymer to degradation by AO. In particular, polyhedral oligomeric silsesquioxanes (POSS™) added within a polymer matrix have been shown to greatly enhance resistance of the polymer to attack by AO. There are examples of OS moieties being added/incorporated into high molecular weight and thermally stable polymer materials; however, there are no previous reports where erosion by exposure to AO was completely stopped as in the current invention.

Wright et al. first disclosed the synthesis of a POSS-diamine and its use in preparing polyimide oligomers in the article titled "The Synthesis and Thermal Curing of Aryl-Ethynyl Terminated coPOSS Imide Oligomers: New Inorganic/Organic Hybrid Resins" (*Chemistry of Materials* 2003, 15(1), pp 264-268). In latter work, Tomzcak et al. used that same POSS diamine to prepare related polyimides that were tested in LEO for durability against AO. Synthesis of the diamine-POSS structure is a multistep process and requires expensive reagents. Furthermore, at high POSS loadings phase separation occurred in the polyimide and unidentified "solids" appeared in the polymer films.

Svejda et al. in U.S. Pat. No. 6,767,930 describes general methods for incorporating POSS structures into polymer matrices using both reactive methods and guest-host approaches. In this patent the authors demonstrate the value of OS in slowing polymer degradation when exposed to AO.

Lichtenhan et al. in U.S. Pat. No. 6,933,345 put forth several scenarios for POSS incorporation into polymeric materials, both as guest-host and as part of a polymer structure. Specific examples and experimental conditions are not given as well as polymer properties (expected or measured). No methods are given for synthesizing an aromatic OS-diamine or POSS-diamine.

In work by Leu et al., "Synthesis and Dielectric Properties of Polyimide-Tethered Polyhedral Oligomeric Silsesquioxanes (POSS) Nanocomposites via POSS-diamine" (*Macromolecules* 2003, 36, pp 9122-9127) they describe making POSS-polyimides and at relatively low levels of incorporation phase separation (self-assembly) occurred in the polyimide leading to a significant drop in glass transition, increase in coefficient of expansion, and a significant decrease in the material strength.

Leu et al. also describe an approach in "Polyimide-Side-Chain Tethered Polyhedral Oligomeric Silsesquioxane Nanocomposites for Low Dielectric Film Applications" *Chemistry of Materials* 2003, 15, pp 3721-3727) by which the POSS structure is incorporated by modifying a fluorinated-polyimide backbone. This requires the polyimide be soluble in organic solvents so lower molecular weight (Mn of 15,000) materials must be utilized. This work was also reported in US patent application 2006/0122350 by Wei et al.

Wright et al. documented new methodology for tethering octahedral silsesquioxanes to soluble polyimides in the article "Chemical Modification of Fluorinated Polyimides: New Thermally Curing Hybrid Polymers with POSS" (*Macromolecules* 2006, 39, pp 4710-4718). In this paper the authors demonstrate very high loadings of POSS to low molecular weight polyimides and demonstrate that in lab testing films show resistance to erosion by AO. The work requires soluble polyimides, multiple separations of polymer/reactants, and utilizes a specialty monomer that is not commercially available.

Poe and Farmer in U.S. Pat. No. 7,619,042 (2009) describe a new method for modifying a soluble polyimide material of low molecular weight similar to that described by Wright et al. In the patent they provide a single example of a fluorinated low molecular weight polymer with no characterization of the OS-containing polymeric materials with regard to purity, physical, mechanical, and/or AO resistance.

It is to be understood that the foregoing is exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Figure 1:
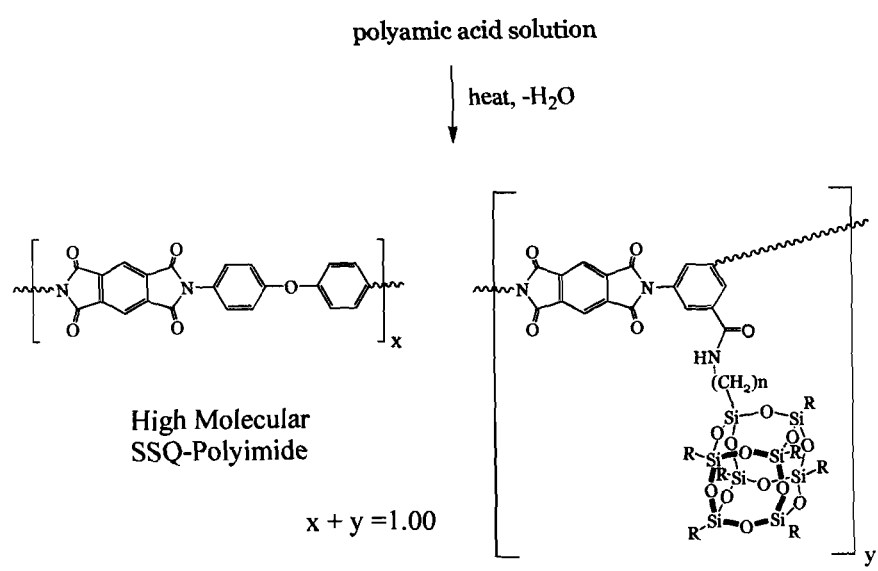
FIG. 1 is a chemical structure of high molecular weight an OS-Polyimide, according to embodiments of the invention.

In an aspect of embodiments, the invention generally relates to an oligomeric silsesquioxane-dinitro aromatic compound having the general formula, including where R are organic substituents, $R^1$ is an alkyl or aromatic organic linker, X is selected from the

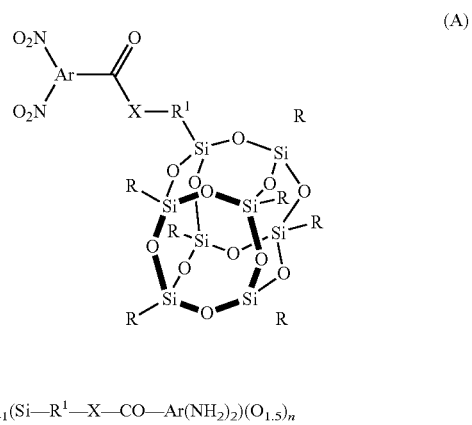

(A)

$(RSi)_{n-1}(Si-R^1-X-CO-Ar(NH_2)_2)(O_{1.5})_n$ linker, X is selected from the group consisting of oxygen, NH, NR, and Ar is a mono- or poly-aromatic system, n is an integer between 6 and 12; dissolving $(RSi)_{n-1}(Si-R^1-X-CO-Ar(NO_2)_2)(O_{1.5})_n$ (A) in a solvent system of tetrahydrofuran and from about 1 vol-% to about 100 vol-% ethanol; adding platinum dioxide or other transition metal hydrogenation catalysts under an atmosphere of hydrogen; allowing contact of reactants until hydrogenation is complete; and isolating $(RSi)_{n-1}(Si-R^1-X-CO-Ar(NH_2)_2)(O_{1.5})_n$ (B), from a solvent system by filtration using a paper filter or equivalent; and where the OS structure is a oligomeric silsesquioxane structure.

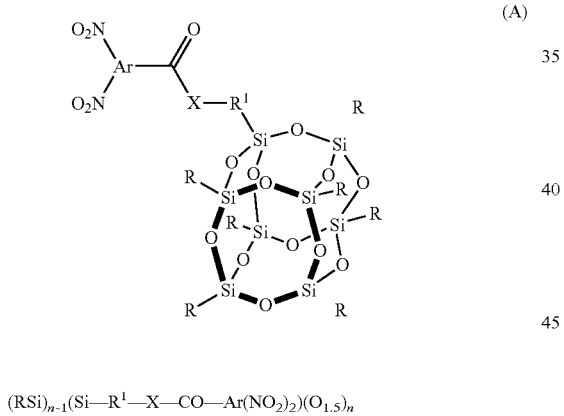

(A)

$(RSi)_{n-1}(Si-R^1-X-CO-Ar(NO_2)_2)(O_{1.5})_n$ group consisting of oxygen, NH, NR, and Ar that is a mono- or poly-aromatic system, n is an integer between 6 and 12; and wherein the OS structure is a oligomeric silsesquioxane structure. In an embodiment, the OS structure is a polyhedral shape where n=8 but not limited to that shape.

In another aspect of embodiments, the invention generally relates to a method for making a oligomeric silsesquioxane-diamine aromatic compound having the general formula, including wherein R are organic substituents, $R^1$ is an alkyl or aromatic organic

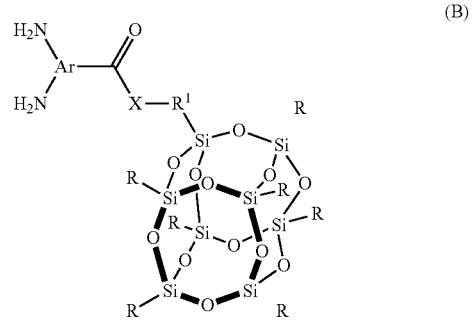

(B)

OS-diamine

In an embodiment, the OS structure is an open structure or a polyhedral shape where n=8. The method embodiments may further include making an oligomeric silsesquioxane-poly(amic acid) which includes dissolving a predetermined amount (ranges of about 1 gram to about 1 kilogram) of said diamines in a predetermined amount of dipolar aprotic solvent (ranges of about 3 grams to about 3 kilograms) with stirring under a nitrogen atmosphere to form a first solution; adding the first solution to a predetermined amount of 4,4'-oxydianiline (ODA) (ranges of about 1 gram to about 1 kilogram) under a nitrogen atmosphere and stirring to allow contact of reactants to form a second solution; suspending a predetermined amount a bis(anhydride) (ranges of about 1 gram to about 1 kilogram) like 1,2,4,5-benzenetetracarboxylic dianhydride in N,N-dimethyl acetamide to form a slurry; adding the slurry by aliquots to the second solution under a nitrogen atmosphere with stirring to allow contact of reactants to form a stable intermediate OS-poly(amic acid) solution; and producing a series of OS-diamine monomers. The method embodiments may further includes preparing poly (amic acids) from the OS-diamine monomers (C).

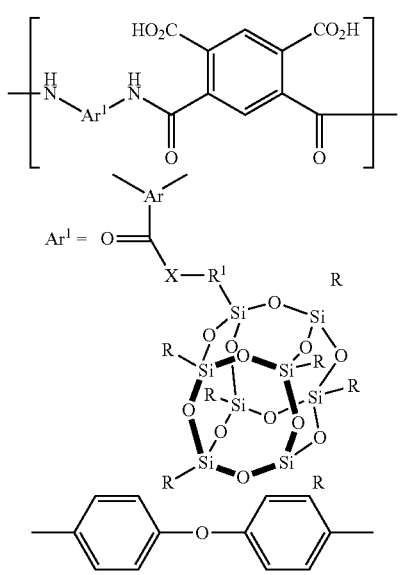

Embodiments of the invention include the diamines being suitable for use including 4,4'-oxydianiline which are selected from the group consisting of 4,4'-diaminodiphenyl propane; 4,4'-diamino-diphenyl methane; benzidine; 3,3'-dichlorobenzidine; 4,4'-diamino-diphenyl sulfide; 3,3'-diamino-diphenyl sulfone; 4,4'-diamino-diphenyl sulfone; 4,4'-diamino-diphenylether; 1,5-diamino naphthalene; 4,4'-di-amino-diphenyl diethylsilane; 4,4'-diamino-diphenyl diphenylsilane; 4,4'-diamino-diphenyl ethyl phosphine oxide; 4,4'-diamino-diphenyl phenyl phosphine oxide; 4,4'-diamino-diphenyl N-methyl amine; 4,4'-diamino-diphenyl N-phenyl amine; and other similar diamines. Embodiments, may also include the dianhyrides suitable for use including pyromellitic dianhydride are selected from the group consisting of 2,3,6,7-naphthalene tetracarboxylic dianhydride; 3,3', 4,4'-diphenyl tetracarboxylic dianhydride; 1,2,5,6-naphthalene tetracarboxylic dianhydride; 2,2',3,3'-diphenyl tetracarboxylic dianhydride; 2,2-bis(3,4-dicarboxyphenyl) propane dianhydride; bis(3,4-dicarboxyphenyl)sulfone dianhydride; perylene 3,4,9,10-tetracarboxylic acid dianhydride; bis(3,4-dicarboxyphenyl)ether dianhydride; naphthalene-1,2,4,5-tetracarboxylic dianhydride; 2,2-bis(2,3-dicarboxyphenyl)propane dianhydride; 1,1-bis(2,3-dicarboxyphenyl) ethane dianhydride; 1,1-bis(3,4-dicarboxyphenyl)ethane dianhydride; bis(2,3-dicarboxyphenyl)methane dianhydride; bis(3,4-dicarboxyphenyl)methane dianhydride; benzene-1,2,3,4-tetracarboxylic dianhydride; pyrazine-2,3,5,6-tetracarboxylic dianhydride; thiophene-2,3,4,5-tetracarboxylic dianhydride; 3,4,3',4'-benzophenone tetracarboxylic dianhydride; and other similar dianhydrides. Several dipolar aprotic solvents having functional groups that are inert to reaction with dianhydrides and diamines including N-methyl-2-pyrrolidinone (NMP), dimethyl sulfoxide (DMSO), N,N-dimethyl acetamide (DMAc), and dimethylformamide (DMF) work well in making the poly(amic acid) solutions, with using DMAc or NMP the preferred solvents.

Embodiments may include the poly(amic acid) solutions further including treating the poly(amic acid) solutions with carbon nanotubes being single wall- and/or multiwall- in loadings of about 0.1 to about 0.7% wt-% based on final polyimide structure; and processing the polyimide structure into films, fibers, or other 3-dimensional shapes. In embodiments, the poly(amic acid) solutions include other conductive particles to produce conductive OS-polyimide films and structures. Embodiments may further include converting the OS-poly(amic acids) to their corresponding polyimides (D);

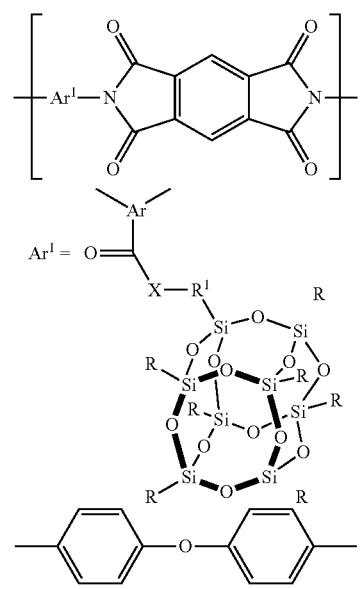

where $Ar^1$ is a combination of OS-diamine and organic diamine wherein said diamines are suitable for use including 4,4'-oxydianiline which are selected from the group consisting of 4,4'-diaminodiphenyl propane; 4,4'-diamino-diphenyl methane; benzidine; 3,3'-dichlorobenzidine; 4,4'-diamino-diphenyl sulfide; 3,3'-diamino-diphenyl sulfone; 4,4'-diamino-diphenyl sulfone; 4,4'-diamino-diphenylether; 1,5-diamino naphthalene; 4,4'-di-amino-diphenyl diethylsilane; 4,4'-diamino-diphenyl diphenylsilane; 4,4'-diamino-diphenyl ethyl phosphine oxide; 4,4'-diamino-diphenyl phenyl phosphine oxide; 4,4'-diamino-diphenyl N-methyl amine; 4,4'-diamino-diphenyl N-phenyl amine; and other similar diamines. In other embodiments the dianhyrides suitable for use including pyromellitic dianhydride are selected from the group consisting of 2,3,6,7-naphthalene tetracarboxylic dianhydride; 3,3',4,4'-diphenyl tetracarboxylic dianhydride; 1,2, 5,6-naphthalene tetracarboxylic dianhydride; 2,2',3,3'-diphenyl tetracarboxylic dianhydride; 2,2-bis(3,4-dicarboxyphenyl)propane dianhydride; bis(3,4-dicarboxyphenyl)sulfone dianhydride; perylene 3,4,9,10-tetracarboxylic acid dianhydride; bis(3,4-dicarboxyphenyl) ether dianhydride; naphthalene-1,2,4,5-tetracarboxylic dianhydride; 2,2-bis(2,3-dicarboxyphenyl)propane dianhydride; 1,1-bis(2,3-dicarboxyphenyl)ethane dianhydride; 1,1-bis(3,4-dicarboxyphenyl)ethane dianhydride; bis(2,3-dicarboxyphenyl)methane dianhydride; bis(3,4-dicarboxyphenyl) methane dianhydride; benzene-1,2,3,4-tetracarboxylic dianhydride; pyrazine-2,3,5,6-tetracarboxylic dianhydride; thiophene-2,3,4,5-tetracarboxylic dianhydride; 3,4,3',4'-benzophenone tetracarboxylic dianhydride; and other similar dianhydrides. Embodiments may further include converting the poly(amic acid) using thermal or chemical methods to obtain polyimides like (D). Other embodiments may include the use of the OS-polyimides in creating films, fibers, or other 3-dimensional structures.

Yet another aspect of the invention generally relates to a method for making a oligomeric silsesquioxane-diamine aromatic compound having the general formula, including where R are organic substituents, $R^1$ is an alkyl or aromatic organic linker, X is

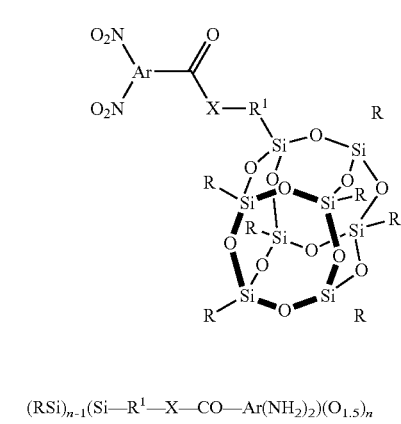

(A)

$(RSi)_{n-1}(Si—R^1—X—CO—Ar(NH_2)_2)(O_{1.5})_n$ selected from the group consisting of oxygen, NH, NR, and Ar is a mono- or poly-aromatic system, n is an integer between 6 and 12; dissolving the $(RSi)_{n-1}(Si—R^1—X—CO—Ar(NO_2)_2)(O_{1.5})_n$ (A) in a solvent system of tetrahydrofuran and from about 1 vol-% to about 100 vol-% ethanol; adding platinum dioxide or other group 8 to group 10 transition metal catalyst under an atmosphere of hydrogen; allowing contact of reactants until hydrogenation is complete; and isolating $(RSi)_{n-1}(Si—R^1—X—CO—Ar(NH_2)_2)(O_{1.5})_n$ from the solvent system by filtration.

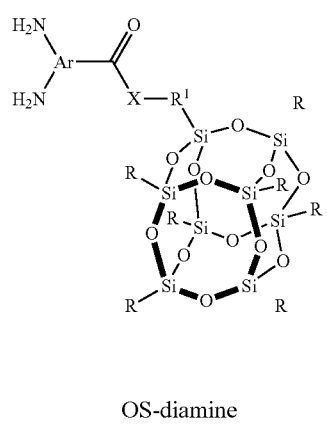

(B)

OS-diamine

In an embodiment, the OS structure is a polyhedral shape where n=8 but can also be an integer between 6 and 12. Embodiments may further include reacting the OS-diamines and other diamines with bis(acid chlorides) to create high molecular weight OS-polyamides.

Yet still another aspect of the invention generally relates to a method for making a oligomeric silsesquioxane-diamine aromatic compound having the general formula, including where R are organic substituents, $R^1$ is an alkyl or aromatic organic linker, X is

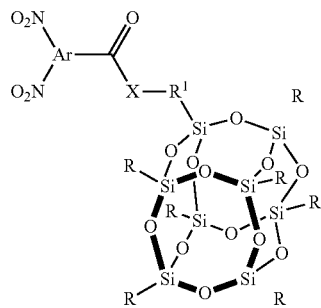

(A)

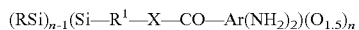

$(RSi)_{n-1}(Si—R^1—X—CO—Ar(NH_2)_2)(O_{1.5})_n$ selected from the group consisting of oxygen, NH, NR, and Ar is a mono- or poly-aromatic system, n is an integer between 6 and 12; dissolving $(RSi)_{n-1}(Si—R^1—X—CO—Ar(NO_2)_2)(O_{1.5})_n$ (A) in a solvent system of tetrahydrofuran and from about 1 vol-% to about 100 vol-% ethanol; adding platinum dioxide or other group 8 to group 10 transition metal catalyst under an atmosphere of hydrogen; allowing contact of reactants until hydrogenation is complete; and isolating $(RSi)_{n-1}(Si—R^1—X—CO—Ar(NH_2)_2)(O_{1.5})_n$ (B) from the solvent system by simple filtration.

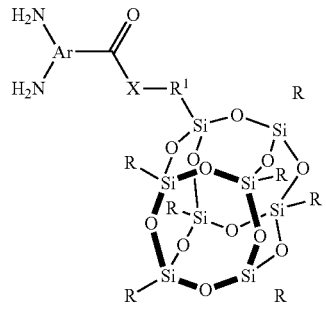

(B)

OS-diamine

In an embodiment, the OS structure is where n=8. Embodiments may further include reacting the OS-diamines and other diamines with bis(epoxides) to form high molecular weight OS-epoxy resins. Embodiments may also include the use of the OS-epoxy resins is to form and process composite panels and other 3-dimensional shapes that include carbon- and/or glass-fabrics.

OS-Diamine Monomer Syntheses

New and highly efficient synthetic routes to an array of new OS-containing monomers are disclosed that can be incorporated into a variety of polymeric materials that exhibit unprecedented resistance to erosion by singlet oxygen/atomic oxygen (AO). The example below is an example of silsesquioxane that can be described in general as an oligomeric silsesquioxane (OS) structure discussed herein is $R_7Si_8O_{12}$, the present disclosure has equal application to any OS cage structure, can include $R_5Si_6O_9$, $R_9Si_{10}O_{15}$, $R_{11}Si_{12}O_{18}$, as well as $R_7Si_8O_{12}$, and any fragment or combination thereof where the formula is $[(R_{(n-1)})(SiO_{1.5})_n$ that is covalently attached (tethered) to an $R_1$ fragment that contains an amino or alcohol functional group. Chemical reaction of the oligomeric silsesquioxane moiety with a suitable dinitro substituted aromatic acid chloride affords in high yield a dinitro-functionalized oligomeric silsesquioxane:

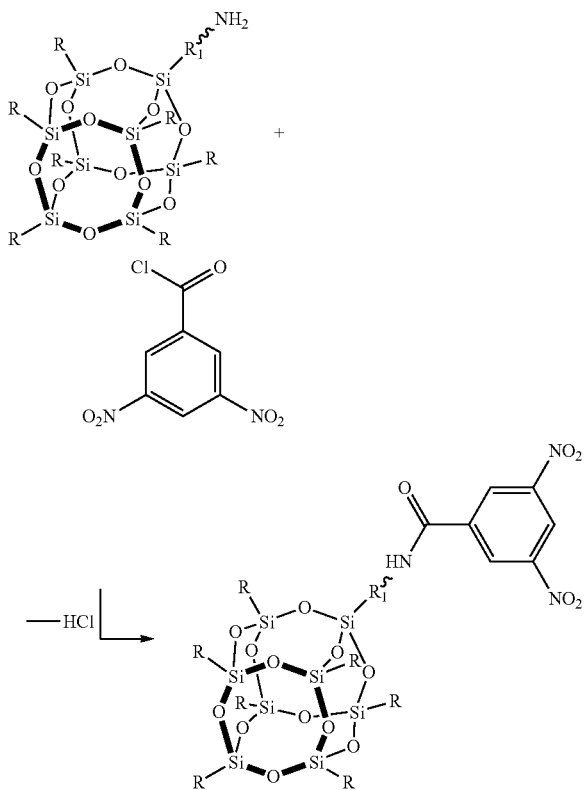

Successful reduction of the nitro groups to their respective aromatic amines must be carried out using selective and mild reaction conditions. The oligomeric silsesquioxane chemical architecture can be very susceptible to degradation and/or rearrangements when dissolved in organic solvents. The reduction reaction/process described in this invention relies on the use of transition metal catalysts, primarily late-transition metals (i.e. group-8 through group-10), the use of low hydrogen pressures (typically 1 to 100 psig), and co-solvents to aid in removal of the transition metal catalyst. Because of the mild reaction conditions alcohol co-solvents (1-100 volume-%) were found advantageous for causing the metal catalyst to aggregate at completion of the reaction that lead to facile and complete removal of catalyst by simple filtration:

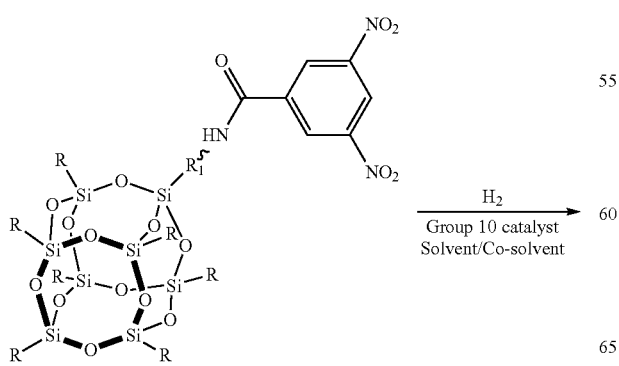

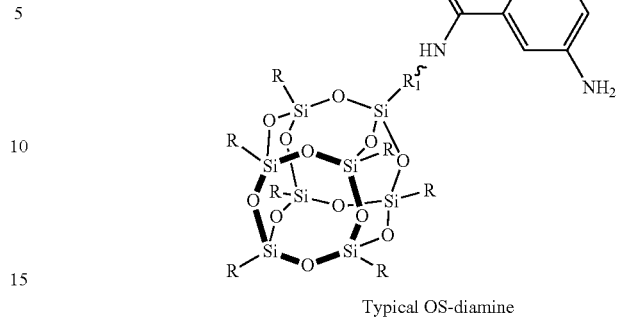

Typical OS-diamine

Disclosed is the copolymerization of the OS-diamines to form high molecular weight aromatic-polyimides, -polyamides, and -epoxies. As discussed in the following, the copolymerization of OS-diamines into high molecular weight aromatic polyimides successfully imparts remarkable and unprecedented AO resistance. Using OS-diamines in the present invention results in only modest differences in the storage modulus, glass transition temperature ($T_g$), and coefficient of thermal expansion (CTE) for the OS-modified polyimides, polyamides, and epoxies.

Aromatic-Polyimides, -Polyamides, and -Epoxies

Polyimides are prepared by reaction of a diamine(s) with a stoichiometric equivalent amount of a bis(anhydride)(s), typically in some dipolar aprotic solvent to afford a poly(amic acid) solution. The latter is used to fabricate structures (e.g. films, panels and fibers) that are then cured by heating. For many aromatic-polyimides this is required since the aromatic-polyimide is insoluble and cannot be melt-processed. The heating removes solvent with concurrent conversion of the poly(amic acid) to the polyimide via a dehydration reaction (loss of water). For aromatic-polyimides, this sequence permits formation and use of high-molecular weight polymers and this is pivotal for obtaining maximum material performance (e.g. tensile and flexural strength) that is required by many applications.

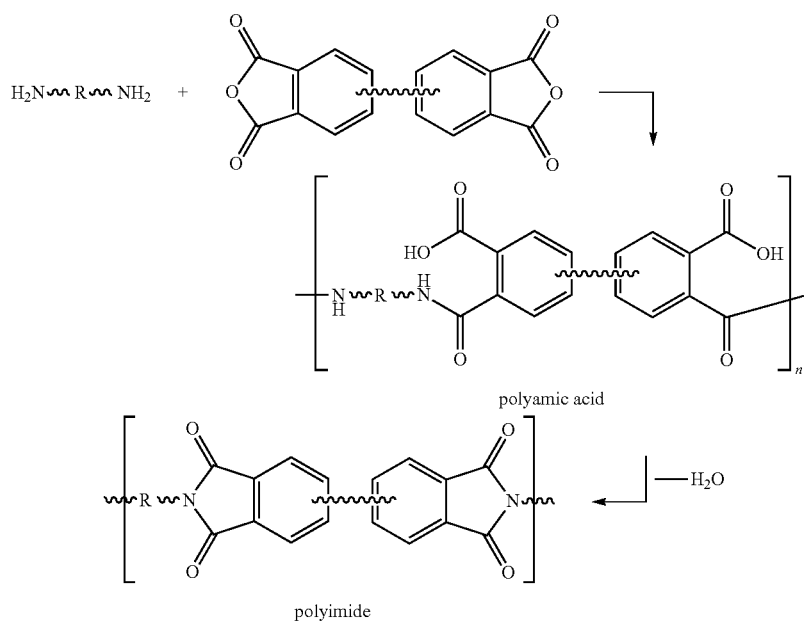

For generating high molecular weight polyimides, critical to high film strength, the OS-diamines prepared above can be co-reacted with other diamines (like 4,4'-diaminophenylether, common name ODA) with a proper (i.e. stoichiometric) amount of an aromatic bis(anhydride) to form a poly (amic acid). The poly(amic acids) are generally formed using a solvent such as N,N-dimethylacetamide, N-methylpyrrolidinone, or other aprotic dipolar solvents:

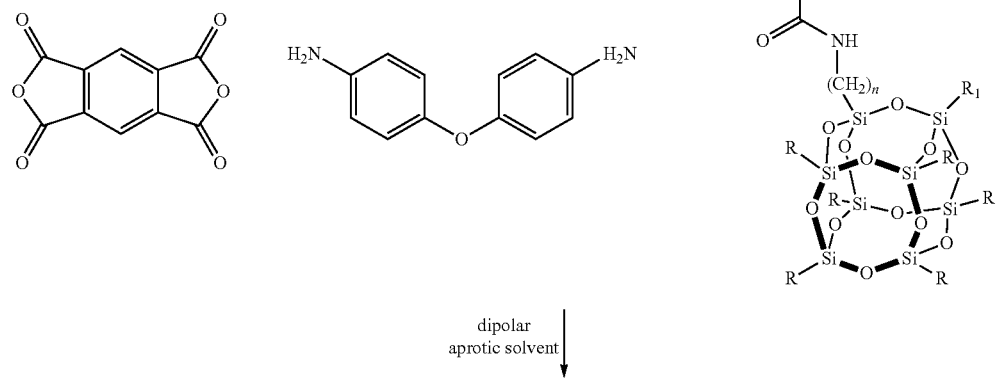

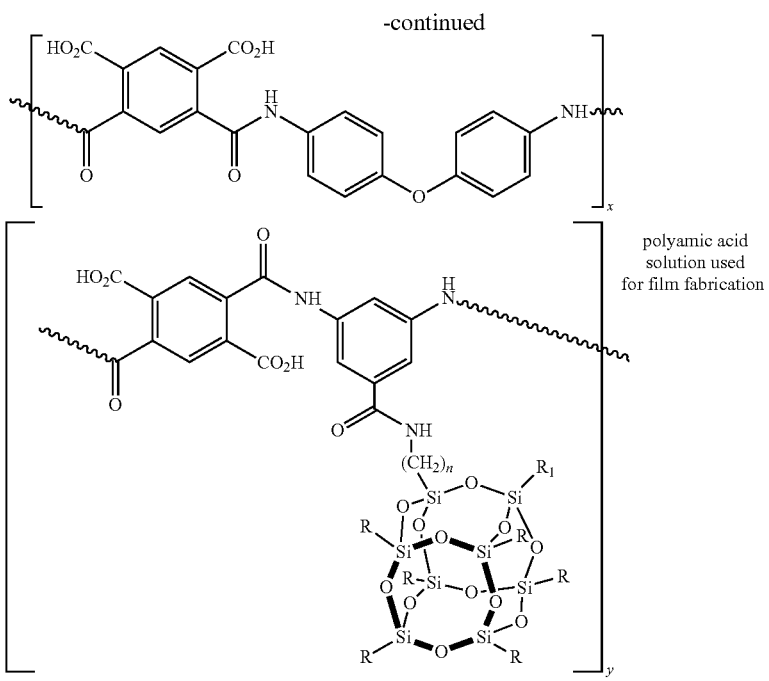

polyamic acid solution used for film fabrication

The OS-poly(amic acid) solutions have been found to be chemically stable for many months (>24) depending on the quality of storage methods (i.e. temperature and isolation from contaminants). The poly(amic acid) solutions can be used to cast films that can be processed by heating into free-standing high molecular weight OS-polyimide films:

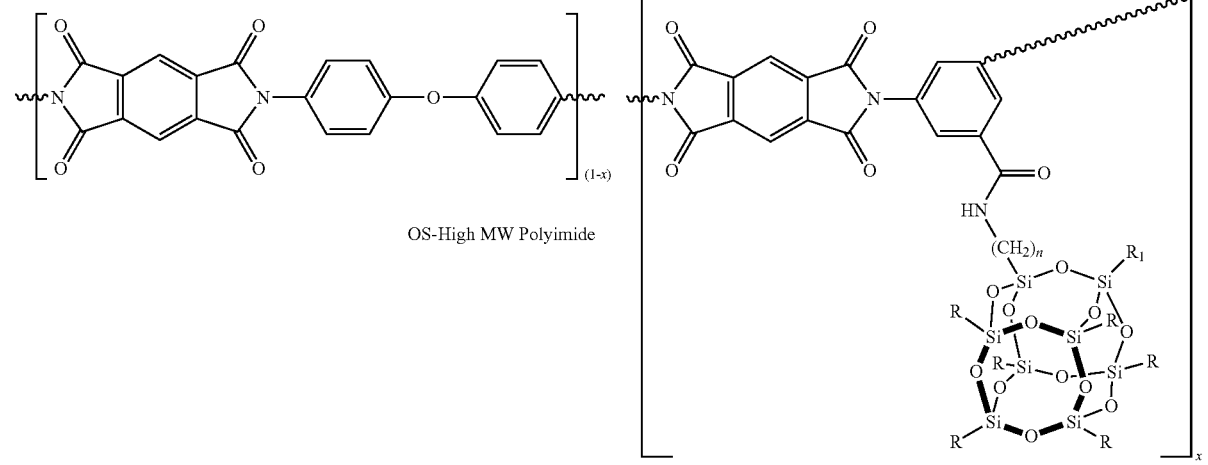

The sudden temperature changes experienced by materials in the LEO environment make the coefficient of thermal expansion an important material property. Mismatches in the CTE between polymeric materials and their coatings lead to cracks, crazing, and mechanical material failure. Conventionally, Kapton® is often coated with silica to resist AO, and may be coated with metal oxides as well to prevent the effects of electrostatic charge differentials on spacecraft surfaces. Multilayer insulation blankets for spacecraft include Kapton® coated with aluminum on the underside and silica on the top surface. These layered systems increase the importance of knowledge of CTE values of OS (including POSS) containing Kaptons®, and their similarity to values for Kapton® materials currently used in space-craft systems.

The OS-Kapton equivalents prepared in this invention may be prepared having higher OS wt-% loadings than compared to previous literature and patent examples for high molecular weight materials. Since high molecular weight is required to make tough films that are in fact capable of delivering sufficient mechanical properties, this result represents an outstanding, demonstrated, and unique feature of this invention.

Aromatic polyamide formation reactions typically involve reactions with bis(acid chlorides) or bis(esters) with a aromatic diamine(s). Mixtures of monomers can be used to tailor the physical and mechanical properties of the resultant polymeric material. For maximum molecular weight the diamine stoichiometry should be equal to the bis(ester) or bis(acid chloride). Use of end-cap or imbalanced stoichiometry can be used to lower molecular weight of the final polymer and this leads to a concomitant loss in mechanical properties.

lar weight for the final polymeric material. In addition, separation of by-products can prove to be difficult and/or impossible.

Coefficient of Thermal Expansion, Mechanical Properties, and Atomic Oxygen Resistance Rapid temperature changes such as those that occur in the space environment give importance to the differences in the CTE between polymer films and their coatings. The CTE of fused silica is about 0.55 ($\mu$m/m° C.). Whether the silica layer is deposited, as with state-of-the-art space materials, or self-generated as with POSS or other OS-polyimides, this mis-

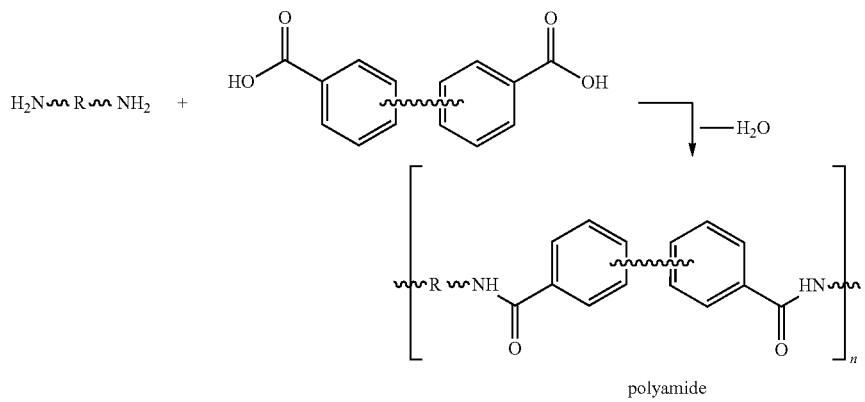

polyamide

Aromatic epoxy resins are a result of an aromatic diamine reacting with a bis(epoxide). These materials must be shaped/processed during the cure reaction since once fully reacted, they are insoluble materials and cannot be melt-processed. What is vital for complete cure of an aromatic epoxy resin formulation is that the aromatic diamine must be compatible with the bis(epoxide) and the resin mixture during the entire cure process. If this is not the case, phase separation will take place and the resulting material will exhibit poor resin properties (both physical and mechanical).

match between the silica passivation layer and the underlying Kapton® is likely to cause cracking and flaking of the silica layer. If this occurs with OS-polyimides, then a fresh silica passivation layer is formed in the areas where cracks or damage have caused the loss of the previously formed silica. This silica regeneration process continually protects the underlying polymer matrix from further reaction/degradation by AO.

The OS-diamines prepared in this invention provide a means of obtaining very high loading of OS in a high molecular weight polymeric material. Results using the OS-diamines

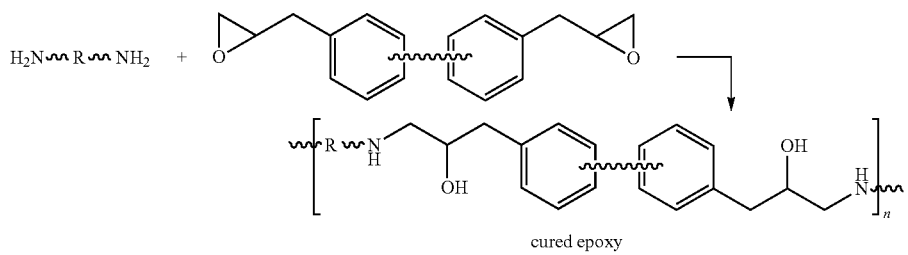

cured epoxy

Incorporation of Functional Molecules in a Polymer Matrix

Several methods exist for adding functionalized molecules within a polymeric material. They can be broken down into categories of 1) guest-host and 2) that of covalent attachment. The former can be quite useful and is the simplest method of incorporation. However, guest-host methods can suffer from phase separation and migration/leaching of the material to the point that bulk polymer properties are compromised. Covalent attachment of a functional molecule can be achieved by 1) use of functionalized monomers or 2) post modification of an existing polymer to create a site of covalent attachment. The latter method requires the polymer be soluble and in the case of aromatic polymers this can severely limit the molecuof this invention show the typical relation of improved resistance to AO as the concentration of OS increases; however, as a result of the present invention producing free standing films that can contain an unexpectedly high OS-loading, the present invention has provided films with 0% erosion rate upon exposure to AO under test conditions that simulate exposure to AO in LEO (TABLE II).

Addition of Conductive Particles to OS-Polyimides

It is known that low levels of carbon nanotube (CNT) incorporation affords polyimide films with conductivity values (i.e. >$10^{-8}$ S/cm) that are sufficient to avoid damage from static electricity build-up or rapid discharge. Thus, to provide a combined resistance to damage from both atomic oxygen and static discharge, we have demonstrated that multi-wall carbon nanotubes (mwCNTs) and other conductive particles can be readily dispersed into selected OS-Kapton polyimides. Notably, it was found the mwCNTs did not have to be chemically treated in order to provide uniform dispersion within the high molecular weight OS-polyimide films. As the particle loading increases there is a corresponding decrease in optical transparency for the films.

Having described the invention, the examples are provided to illustrate specific applications of the art and provide ample guidance to carry out and perform the invention. These specific examples are not intended to limit the scope of the invention described in this application.

EXAMPLE 1

To a stirring suspension of 3,5-dinitrobenzoic acid (0.50 g, 2.36 mmol) in dichloromethane ($CH_2Cl_2$) (10 mL) was added oxalyl chloride ($C_2O_2Cl_2$) (1.23 mL, 2.46 mmol, 2M in dichloromethane. Dimethylformamide (DMF) (1 drop) was added and the mixture immediately began to effervesce. The mixture became homogeneous and effervescence decreased over the course of 45 min. with stirring continued for a total of 1.5 h. A separate flask was charged with (3-aminopropyl) hetpa-isobutyl$Si_8O_{12}$ (1.87 g, 2.14 mmol), dichloromethane (10 mL) and triethylamine ($N(CH_2CH_3)_3$) (0.45 mL, 3.21 mmol) in that order and cooled to 0° C. with stirring. The acid chloride solution was cannulated into the chilled amine solution; the flask containing the acid chloride was treated with an additional 2 mL of dichloromethane and again cannulated into the amine solution. The reaction mixture was allowed to stir for 2.5 hr at 0° C. then diluted with ether (150 mL). The organic phase was washed with saturated aqueous sodium bicarbonate ($NaHCO_3$) (2×150 mL), brine (1×100 mL), dried over magnesium sulfate ($MgSO_4$), filtered and concentrated under reduced pressure to yield N-[3-(hepta-isobut $Si_8O_{12}$)propyl]-3,5-dinitrobenzamide as a pale yellow solid (2.29 g, ~100%). $^1$H NMR ($CDCl_3$) δ 9.16 (t, J=2.1 Hz, 1H), 8.91 (d, J=2.1 Hz, 2H), 6.33 (br t, 1H, NH), 3.52 (appt q, 2H), 1.95-1.69 (m, 9H), 0.96-0.93 (m, 42H), 0.65-0.55 (m, 14H); $^{13}$C NMR ($CDCl_3$) δ 162.6, 148.7, 138.2, 127.0, 121.0, 43.1, 25.7, 25.4, 23.9, 23.8, 22.9, 22.5, 9.6. Anal. Calcd for $C_{38}H_{70}N_3O_{17}Si_8$: C, 42.83; H, 6.62. Found: C, 42.73; H, 6.80.

EXAMPLE 2

A Schlenk flask was charged with N-[(hepta-isobutyl-$Si_8O_{12}$)propyl]-3,5-dinitrobenzamide (1.5 g, 1.40 mmol), $PtO_2$ (150 mg), and ethanol (40 mL). The Schlenk flask was charged with $H_2$ (about 2 psig, 4 pressure/evacuation/backfill cycles) and allowed to react with stirring for 8 h. The mixture was filtered through a very fine filter medium such as diatomaceous earth (Celite®) and the solvent was removed under reduced pressure to yield N-[3-(hepta-isobutyl)$Si_8O_{12}$)propyl]-3,5-diaminobenzamide as an off-white solid (1.35 g, ~95% yield). $^1$H NMR ($CDCl_3$): δ 6.43 (d, J=2.0 Hz, 2H), 6.10 (t, J=2.0 Hz, 1H), 5.96 (br t, 1H, NH), 3.66 (br s, 4H, $NH_2$), 3.39 (br appt q, 2H), 1.95-1.74 (appt. septant, 7H), 1.71-1.62 (m, 2H) 0.96 (br s, 21H), 0.93 (br s, 21H), 0.69-0.63 (m, 2H), 0.61 (d, J=1.8 Hz, 7H), 0.57 (d, J=1.8 Hz, 7H). $^{13}$C NMR ($CDCl_3$): δ 168.0, 147.7, 137.5, 104.3, 103.9, 42.2, 25.7, 23.9, 23.8, 23.0, 22.49, 22.46, 9.5. Anal. Calcd for $C_{38}H_{77}N_3O_{13}Si_8$: C, 45.25; H, 7.69; N, 4.16. Found: C, 45.13; H, 7.69; N, 4.08.

EXAMPLE 3

N-[3-(hepta-cyclohexyl)$Si_8O_{12}$)propyl]-dinitrobenzamide was prepared using 3-aminopropyl-hepatacyclohexyl$Si_8O_{12}$ by the same procedure as described above for the synthesis of N-[3-(hepta-isobutyl $Si_8O_{12}$)propyl]-3,5-dinitrobenzamide. A Schlenk flask was charged with the N-[3-(heptacyclohexyl $Si_8O_{12}$)propyl]-3,5-dinitrobenzamide (1.40 mmol), $PtO_2$ (150 mg), and ethanol (40 mL). The Schlenk flask was charged with $H_2$ (about 2 psig, 4 pressure/evacuation/backfill cycles) and allowed to react with stirring for 8 h. The mixture was filtered through diatomaceous earth (Celite®) or an equivalent filtration medium and the solvent was removed under reduced pressure to yield N-[(cyclohexyl-POSS)propyl]-3,5-diaminobenzamide (i.e., N-{3-(cyclohexyl$_7$$Si_8O_{12}$)propyl}-3,5-diaminobenzamide)) as an off-white solid.

It will be known to those of ordinary skill in the art that other methods may be used to process the aforesaid organic phase to isolate the above-referenced dinitrobenzamide, as well as to process the aforesaid reaction mixtures to isolate the above-referenced diaminobenzamides, and such processes are within the scope of this disclosure.

EXAMPLE 4

In a $N_2$ filled glovebox, a 25 mL round bottom flask was charged with OS-diamine (N-{3-(hepta-isobutyl$Si_8O_{12}$)propyl}-3,5-diaminobenzamide) (0.3749 g, 0.3719 mmol), a stir bar, and DMAc (2 mL) and the mixture allowed to stir until homogeneous. A second 50 mL round bottom flask was charged with 4,4'-ODA (0.8437 g, 4.21 mmol) and a stir bar. The OS-diamine/DMAc solution was transferred by syringe into the 4,4'-ODA and was stirred. PMDA (1.00 g, 4.59 mmol) was weighed into a 25 mL round bottom flask, and transferred drop-wise by syringe, as a slurry in DMAc, into the diamine mixture over 30 min. A total of 20 mL DMAc was added to the polymer solution. The OS-poly(amic acid) solution) became moderately viscous, and stirred overnight at room temperature. The OS-poly(amic acid) was stored under nitrogen in a freezer, and has been found to produce high quality films via spin-coating or other commonly used film forming techniques after 1 year of storage. Thick films (e.g., 2 mil) were easily produced that were optically clear and flexible. The films show excellent optical clarity and mechanical properties with a $T_g$ approaching 380° C.; hence comparable with Kapton-H which has a $T_g$ of about 400° C. as measured by dynamic mechanical thermal analysis (DMTA).

EXAMPLE 5

OS-poly(amic acid) based on N-{3-(heptacyclohexyl$Si_8O_{12}$)propyl}-3,5-diaminobenzamide monomer, as well as monomers derived from other aminoalkyl $R_7$—OS nanostructures, (0.3719 mmol) have been readily copolymerized with PMDA and ODA in DMAc to generate stable OS-poly(amic acid) solutions via the same method as described above in EXAMPLE 4.

EXAMPLE 6

The OS-diamine monomers disclosed here may also be reacted with bis(epoxides) to form epoxy resins having high POSS loadings (from about 5 wt-% to about 40 wt-%). Epoxy resins having the highest OS loadings are obtained where the "R" substituent on the OS-cage is phenyl. A 25 mL flask was charged with OS-diamine, (N-{3-(hepta-phenyl$Si_8O_{12}$)propyl}-3,5-diaminobenzamide), (2 mmol) and epon 828 resin (2 mmol), and then mixed thoroughly. The mixture was then allowed to cure with mild heating into a shape of choice (dogbone, plate, or other more complicated shapes). A clear and tough epoxy resin article can be generated in this manner.

EXAMPLE 7

The OS-diamines may also be used to prepare polyamides and polyurethanes by reaction with diacid chlorides and bis (isocyanates), respectively, to form tough and high molecular weight coatings. By adding an end-cap (mono-functionalized amine or acid chloride) to the polyamide formulations, soluble oligomers may be prepared with excellent control of the oligomer's molecular weight.

EXAMPLE 8

OS-Diamine monomers of the formula N-{3-($R_7Si_8O_{12}$) propyl}-3,5-diaminobenzamide, where R is one of iso-octyl, methyl, ethyl (or other alkyl), cyclopentyl, phenyl (or other aryl), and trifluoropropyl (or other fluoroalkyl), were copolymerized with 4,4'-oxydianiline (ODA) and 1,2,4,5-benzenetetracarboxylic dianhydride (pyromellitic dianhydride, PMDA) via the same reaction scheme to afford high $T_g$ polyimides having a polymer backbone equivalent to Kapton®. Typically the monomer formulations incorporate enough POSS-diamine to produce a final OS-polyimide that contains about 8 wt % of the $(SiO_{1.5})_8$ cage although much higher loadings can be achieved with the current invention.

EXAMPLE 9

A OS-poly(amic acid) solution, with approximately 20 wt % solids, was poured on a clean glass plate which was balanced in a vacuum oven, equipped with a $N_2$ flow. The DMAc solvent was evaporated at 80° C. for 4 h, followed by a cure schedule of 120° C. for 1 h, 200° C. for 1 h, and 275° C. for 2 h to full cure to a high molecular weight. The amber colored and visibly transparent films were removed from the slide by placing them under running deioinized water, lifting the film corner with a razor blade, and running water between the glass and the film. The films were stored in air.

EXAMPLE 10

Figure 5:
FIG. 5 is an optical micrograph looking edge-on of a OS-Kapton polymer film having 0.5 wt-% mwCNTs after complete cure at elevated temperature, according to embodiments of the invention.

DMAc solutions of the poly(amic acid) OS-Kapton were treated with 0.1 wt % to 0.7 wt % of multi-wall carbon nanotubes (mwCNTs). The solutions were subjected to sonification for about 1 min and then cast into about 50 micron films. No mechanical forces are applied during film formation (i.e. solvent evaporation). The free-standing films of the poly (amic acid) and thermally cured polyimides were then cut, supported in an epoxy matrix, polished, and then analyzed by a special form of microscopy where a detailed analysis in 3-dimensions could be realized. A certain degree of alignment is achieved in the compaction from solvent release. Upon cure, there is an unprecedented amount of mwCNT alignment (FIG. 5).

EXAMPLE 11

OS-Polyimide samples were analyzed using a dynamic mechanical thermal analysis (DMTA) V from TA Instruments with a 5° C./min temperature ramp from room temperature to 500° C. in tensile mode. Coefficient of thermal expansion measurements were taken on a thermomechanical analyzer (TMA 2940) from TA Instruments with a film fiber attachment in a nitrogen atmosphere. The cured films were cut into 15 mm by 3 mm samples, the force applied was 0.05 N & 0.10 N, and the sample was heated at 5° C./min. The CTE was calculated as α=(ΔL×K)/(L×ΔT) where L=length, K=a cell constant, T=temperature in ° C. Test variability was +/−2.306 ppm ° C.$^{-1}$ based on five Kapton® H tests.

As shown in the following, the dynamic and mechanical thermal properties of OS-Kaptons have insignificant differences from Kapton® in the temperature range experienced in LEO (−50° C. to 150° C.).

TABLE I

Coefficients of Thermal Expansion for
Kapton ® and OS-Kapton Films

| Sample | [a]CTE (μm/m° C.)* |
|---|---|
| Kapton H ® (commercial product) | 30.25 |
| 0 wt % OS-Kapton (lab synth. standard) | 33.11 |
| 7 wt % $Si_8O_{12}$ OS-Kapton | 35.86 |
| 7 wt % $Si_8O_{12}$ OS-Kapton exposed to $AO^b$ | 33.64 |

Figure 2:
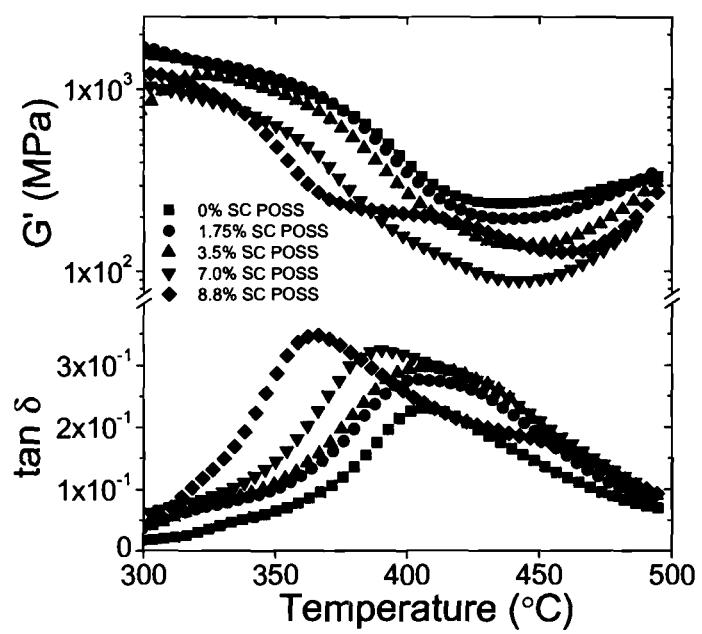
FIG. 2 is a graph showing dynamic mechanical thermal analysis of 0, 1.75, 3.5, 7, and 8.8 weight-% $Si_8O_{12}$ OS-Kapton (SC POSS is OS-Kapton), according to embodiments of the invention.

[a]Test variability based on 5 Kapton H ® tests = ±2.306 ppm/° C.
[b]2.3 × $10^{20}$ oxygen atoms $cm^{-2}$ The physical properties of OS-Kaptons were evaluated by DMTA as shown in FIG. 1 and FIG. 2. As the weight % of the $Si_8O_{12}$ OS-cage increased as follows: 0, 1.75, 3.5, 7, and 8.8, the $T_g$'s decreased as follows: 407° C., 403° C., 406° C., 392° C., and 365° C., respectively. It is likely that increasing the amount of the bulky OS-POSS increases the free volume in the polymer matrix, and decreases the areas dipole-dipole interactions between adjacent polyimide backbone chains.

EXAMPLE 12

Figure 3:
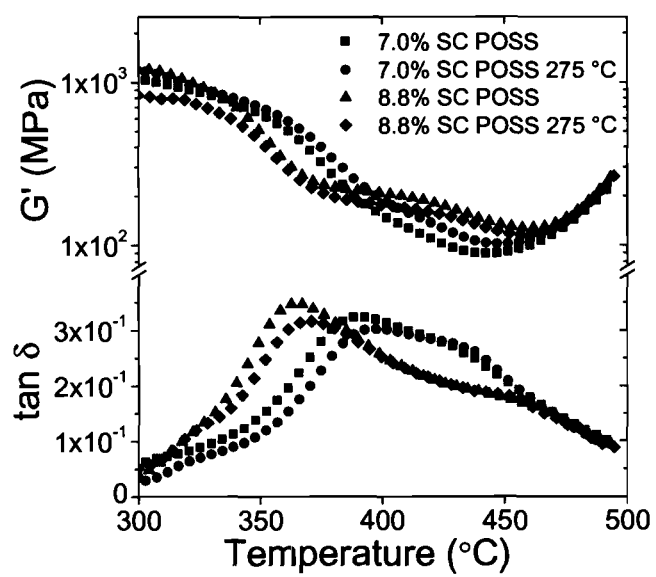
FIG. 3 is a graph showing a dynamic mechanical and thermal analysis of 7 and 8.8 weight % $Si_8O_{12}$ OS-Kapton cured at 275° C. for 2 hours (7.0% OS) and 20 hours (7.0% OS 275° C.) (SC POSS is OS-Kapton), according to embodiments of the invention.
Figure 4:
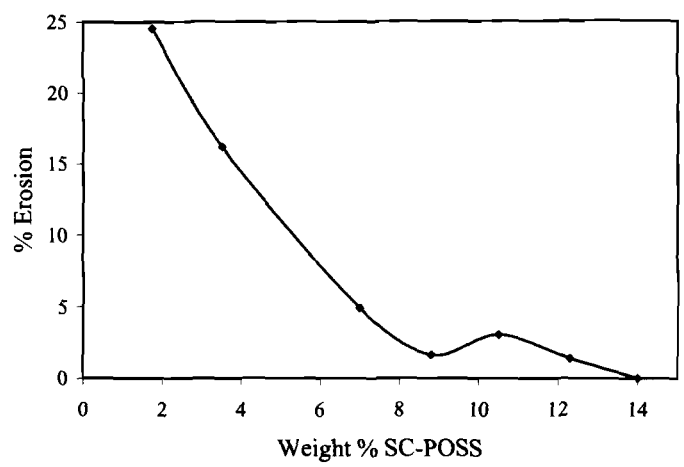
FIG. 4 is a graph showing percent erosion of OS-Kapton/Kapton® witness sample vs weight % $Si_8O_{12}$ OS-Kapton prepared, according to embodiments of the invention. Total fluence: $2.7 \times 10^{20}$ O atoms/cm$^{-2}$. (SC POSS is OS-Kapton), according to embodiments of the invention.

The series of OS-Kaptons was exposed to AO with a total fluence of 2.7×$10^{20}$ O atoms $cm^{-2}$. The results in Table II show a dramatic decrease in surface erosion with increasing POSS content, until undetectable erosion is reached with 14 wt % OS-POSS Kapton. These results are presented graphically in FIG. 3.

TABLE II

AO Erosion Data of OS-Kapton Polyimides

| Weight % $Si_8O_{12}$ in OS-Kapton | Kapton ® Equivalent Fluence/ $10^{20}$ O atoms/$cm^2$ | Erosion Depth (μm) | % Erosion of Kapton H ® Witness Sample |
|---|---|---|---|
| 1.75 | 2.71 | 1.99 ± 0.01 | 24.5 |
| 3.5 | 2.66 | 1.29 ± 0.05 | 16.15 |
| 7.0 | 2.68 | 0.390 ± 0.04 | 4.9 |
| 8.8 | 2.68 | 0.132 ± 0.02 | 1.64 |
| 10.5 | 2.71 | 0.249 ± 0.03 | 3.06 |
| 12.3 | 2.71 | 0.113 ± 0.03 | 1.39 |
| 14.0 | 2.71 | Undetectable | ~0 |

In an AO exposure with a total fluence of 3.53×$10^{20}$ O atoms $cm^{-2}$, 7% $Si_8O_{12}$ OS-Kapton® had an erosion yield that was 3.3% of Kapton H®. These materials were also exposed side by side to 2.68×$10^{20}$ O atoms $cm^{-2}$. The % erosion of the OS-Kaptons® relative to Kapton H® were 4.86±0.47 microns for 7 wt % $Si_8O_{12}$ OS-POSS-Kapton® which compares favorably with the literature to other OS containing polymers. Thus, the level of erosion resistance afforded by OS moieties appears with current data to depend on the wt % of the OS and that is also true in the current invention. The ability to incorporate very high levels of OS (e.g. Table II, 14 wt-% $Si_8O_{12}$) enables the materials described in this invention to achieve unprecedented protection from AO erosion.

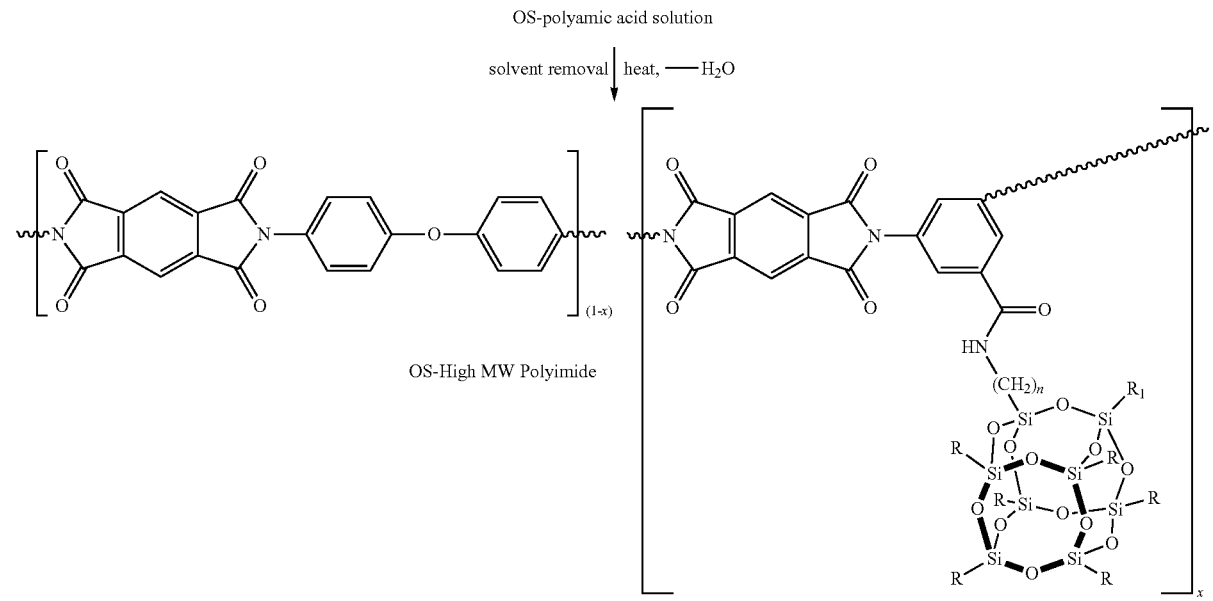

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for making a oligomeric silsesquioxane (OS)-diamine aromatic compound having the general formula, comprising:

$$(RSi)_{n-1}(Si\text{—}R^1\text{—}X\text{—}CO\text{—}Ar(NH_2)_2)(O_{1.5})_n \quad (C)$$

wherein R are organic substituents, $R^1$ is an alkyl or aromatic organic linker, X is selected from the group consisting of NH, NR, and Ar is a mono- or poly-aromatic system, n is an integer ranging between 6 and 12;

dissolving a oligomeric silsesquioxane (OS)-diamine aromatic compound having the general formula, $$(RSi)_{n-1}(Si\text{—}R1\text{-}X\text{—}CO\text{—}Ar(NH2)2)(O1.5)_n \quad (C)$$

wherein R is organic substituents, R1 is an alkyl or aromatic organic linker, X is selected from the group consisting of NH, NR, and Ar is a mono- or poly-aromatic system, n is an integer ranging between 6 and 12;

adding an aliphatic tertiary amine to the said solution of said amino-functional oligomeric silsesquioxane compound;

homogenizing said solution of said amino-functional oligomeric silsesquioxane compound;

adding a solution of an aromatic di-nitro acid chloride to said solution of said amino-functional oligomeric silsesquioxane compound;

allowing the mixture to remain homogeneous and in contact for and effective amount of time sufficient to complete the conversion of acid chloride and amine groups to amide groups forming a compound with the general formula $(RSi)_{n-1}(Si\text{—}R^1\text{—}X\text{—}CO\text{—}Ar(NO_2)_2)(O_{1.5})_n$ (A);

dissolving said $(RSi)_{n-1}(Si\text{—}R^1\text{—}X\text{—}CO\text{—}Ar(NO_2)_2)(O_{1.5})_n$ (A) in a solvent system of ethanol and from about 1 vol-% to about 99 vol-% of tetrahydrofuran;

adding platinum dioxide or transition metal hydrogenation catalysts under an atmosphere of hydrogen at pressures of 1 to 1000 psig; and allowing contact of reactants until hydrogenation is substantially complete to formulate said diamine (C).

2. The method according to claim 1, for the isolating said $(RSi)_{n-1}(Si\text{—}R^1\text{—}X\text{—}CO\text{—}Ar(NH_2)_2)(O_{1.5})_n$ (C), from a solvent system by filtration using a paper filter or equivalent; and wherein the OS structure is a oligomeric silsesquioxane structure.

3. A compound prepared by the method according to claim 1, wherein n=8

(D)
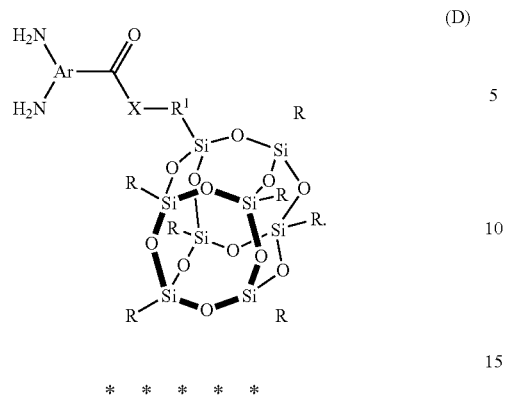
* * * * *